(12) United States Patent
Takahashi

(10) Patent No.: US 8,199,320 B2
(45) Date of Patent: Jun. 12, 2012

(54) MOUNTING TEST METHOD

(75) Inventor: Hideaki Takahashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 342 days.

(21) Appl. No.: 12/534,305

(22) Filed: Aug. 3, 2009

(65) Prior Publication Data

US 2010/0053626 A1    Mar. 4, 2010

(30) Foreign Application Priority Data

Sep. 3, 2008    (JP) .................................. 2008-225900

(51) Int. Cl.
*G01N 21/00*    (2006.01)
(52) U.S. Cl. .................................. 356/237.1; 356/237.6
(58) Field of Classification Search .... 356/237.1–237.6, 356/394, 614–623
See application file for complete search history.

(56) References Cited

U.S. PATENT DOCUMENTS

| 5,083,863 | A | * | 1/1992 | Cerda ........................ 356/237.1 |
| 5,302,819 | A | * | 4/1994 | Kassies ...................... 250/222.1 |
| 2002/0122186 | A1 | * | 9/2002 | Igaki et al. ..................... 356/616 |
| 2008/0085033 | A1 | * | 4/2008 | Haven et al. ................... 382/103 |
| 2009/0213093 | A1 | * | 8/2009 | Bridger ......................... 345/175 |
| 2010/0246894 | A1 | * | 9/2010 | Koike et al. ................... 382/106 |

FOREIGN PATENT DOCUMENTS

| JP | 6-84078 | 3/1994 |
| JP | 2006-324057 | 11/2006 |

* cited by examiner

*Primary Examiner* — Hoa Pham
(74) *Attorney, Agent, or Firm* — Staas & Halsey LLP

(57) ABSTRACT

A method for testing a part mounting status on a substrate, the method comprises preparing the part including a retroreflection portion for occurring reflect light by retroreflection; irradiating light onto the retroreflection portion; receiving the reflect light from the retroreflection portion; and determining whether the part exist by the use of the reflect light from the retroreflection portion.

11 Claims, 19 Drawing Sheets

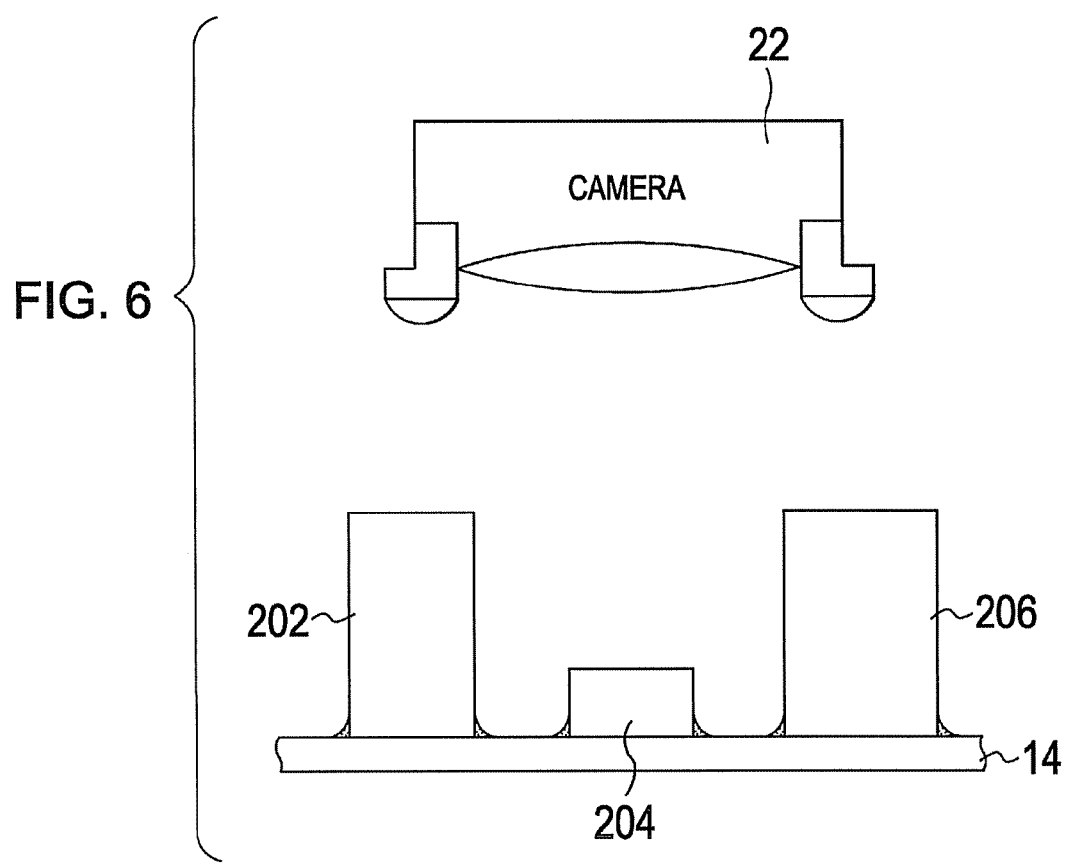

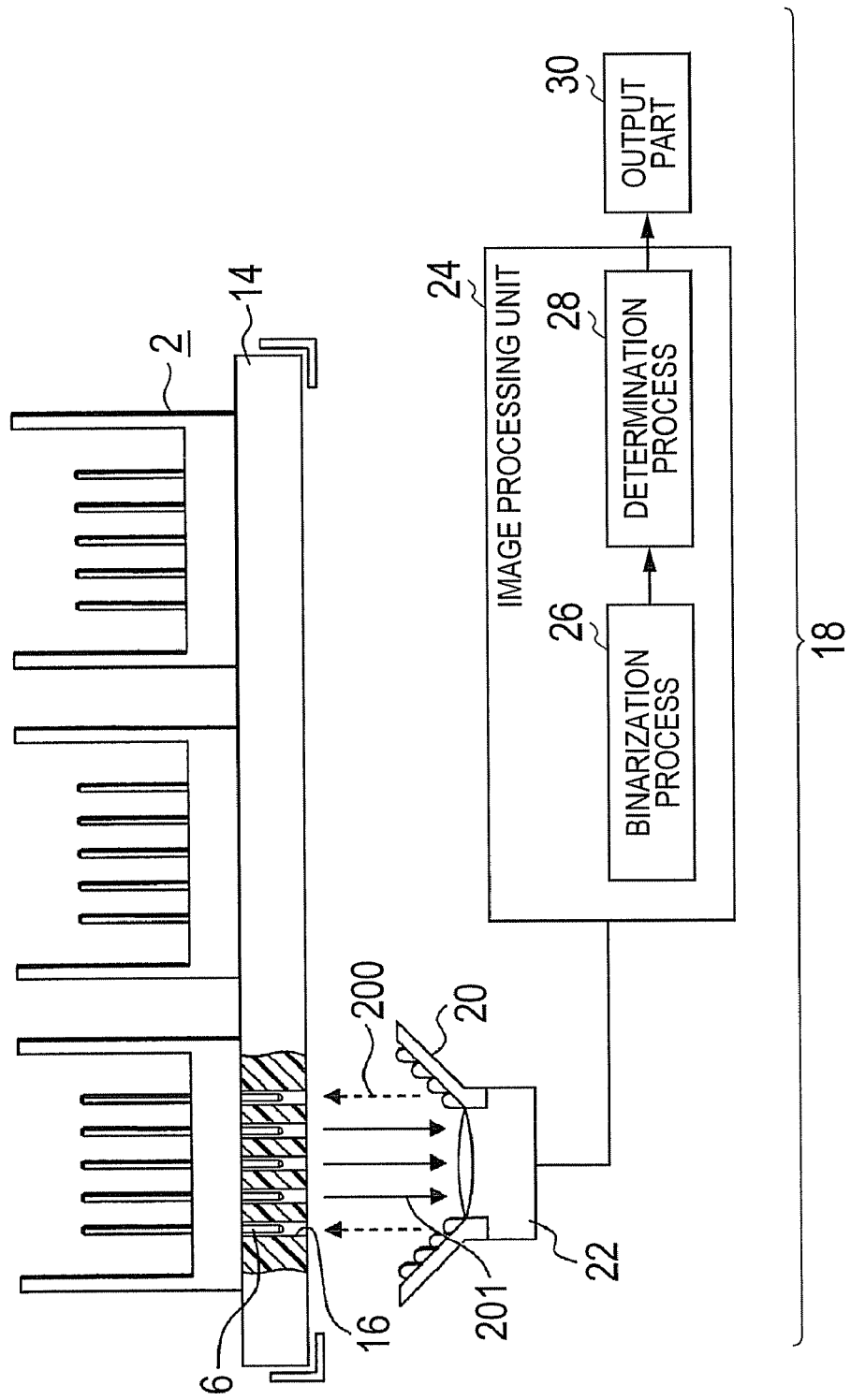

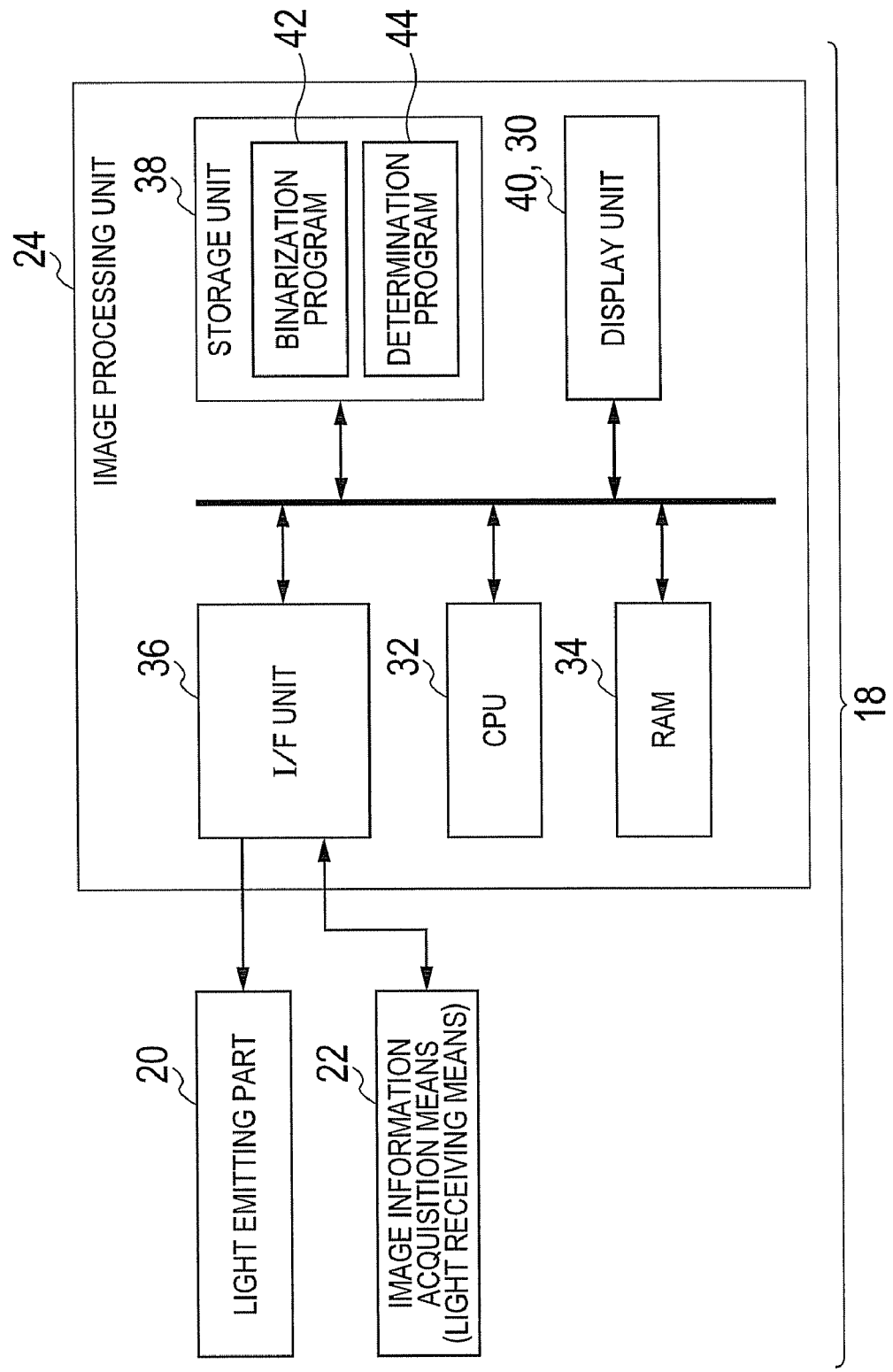

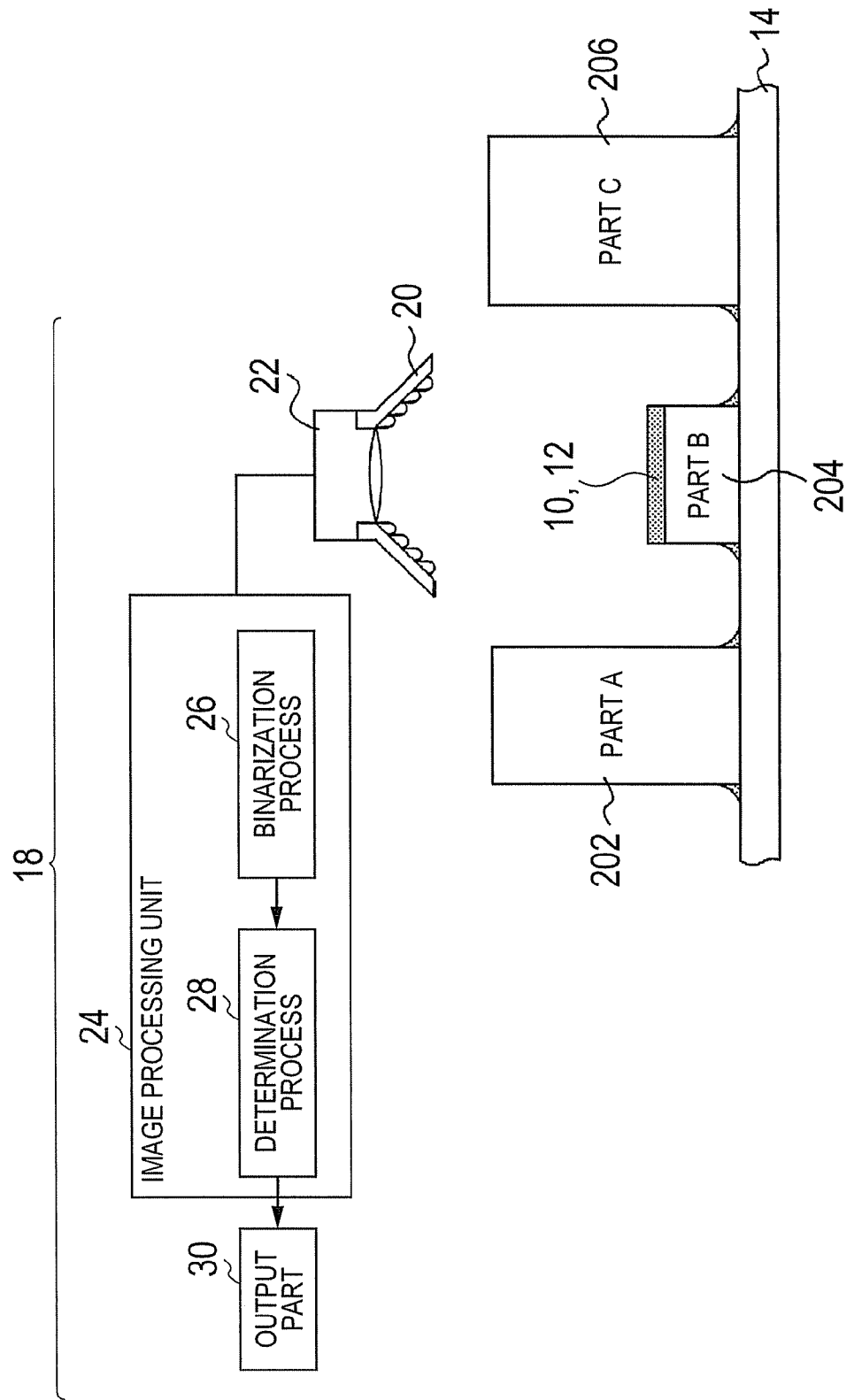

MOUNTING TEST METHOD

CROSS-REFERENCE TO RELATED APPLICATION

This application is based upon and claims the benefit of priority of the prior Japanese Patent Application No. 2008-225900, filed on Sep. 3, 2008, the entire contents of which are incorporated herein by reference.

FIELD

A certain aspect of the embodiments discussed herein is related to a test device for testing mounting status of parts.

BACKGROUND

There is a method for testing by the use of an image device whether a part is properly mounted on, for example, a printed wiring board. For example, it is known that the method includes steps for emitting light onto a part to be tested, for reading with a charge coupled device (CCD) camera, and performing image processing.

A method for performing automatic test by the use of an image of terminals 6 of a press-fit connector 2 that is press-fit exists as a method for checking, by appearances, whether a press-fit connector as an example of a mounted part is correctly pressed into a printed wiring board, as illustrated in FIG. 1A. In this case, an image of the respective tips of the terminals 6 of the press-fit connector 2 pressed into a printed wiring board 14 is captured with a CCD camera by emitting light onto the printed wiring board 14 from the lower surface side thereof to check the mounting status, as illustrated in FIG. 1B and FIG. 1C.

Japanese Laid-open Patent Publication No. 06-084078 (e.g. Abstract, paragraph 0018, and FIG. 1) discuss a test device for a fire detector as a test device in which a retroreflective substrate is used. The test device for a fire detector includes a retroreflective substrate attached to a place corresponding to the viewing angle of a light receiving element. In the test device for a fire detector, a fire detector and the monitoring area may be readily checked by the use of the retroreflective substrate. A test tool is observed from a position at a predetermined height, and it is checked, by the appearance of the retroreflective substrate attached to the test tool, whether a position to be checked is within the monitoring area of the fire detector.

Moreover, Japanese Laid-open Patent Publication No. 2006-324057 (e.g. Abstract, FIG. 4) discuss a method for press-fitting a press-fit connector in which, even when variations in the thickness of a printed wiring board occur, a constant press-fit height of a press-fit connector into terminal holes is maintained. One of the side of press-fit terminals and the side of a printed wiring board or a bus bar in which terminal holes are provided to be set as a fixed side, and the other side is set as a movable side. The movable side is moved up or down toward the fixed side. A contact position between the respective tips of the press-fit terminals and the printed wiring board or the bus bar or a position at a predetermined distance from the contact position is set as a reference position, and a sensor is provided at the reference position. When the sensor detects that the movable side has reached the reference position, the movable side is stopped after being moved a predetermined movement distance from the detection position so as to maintain a constant press-fit height of the press-fit terminals into the terminal holes.

In the printed wiring board 14, due to improvement of the speed of transmission signals, when the terminals 6 of the press-fit connector 2, which is press-fit, protrude from the lower surface side of the printed wiring board 14, as illustrated in FIG. 1A, since the protruding terminals 6 are close to each other, as illustrated in FIG. 1B, noise is picked up, and thus a disadvantage arises in that product characteristics may not be satisfied. FIG. 1C illustrates the magnified appearance of each of the protruding terminals 6, as viewed from the back side of the printed wiring board 14. Thus, an arrangement in which, even in a state in which the press-fit connector 2 is correctly press-fit, the tip of each of the terminals 6 does not protrude from the lower surface of the printed wiring board 14, as illustrated in FIG. 2A, may be adopted.

In a method for emitting light onto a terminal portion as a method for testing the mounting status of a part, when the terminals 6 are set to protrude from the printed wiring board 14, as illustrated in FIG. 3A, the presence or absence of the terminal portion may be checked, as illustrated in FIG. 3B. In contrast, when the terminal portion does not protrude from the printed wiring board 14, as illustrated in FIG. 2A, even in the case of a nondefective product, the emitted light may be weakened because the tip of each terminal is located within a corresponding through hole 16, as illustrated in FIG. 2B. Thus, it is difficult to determine the mounting status on the basis of an obtained image.

Moreover, in the case of a defective product in a state such as buckling because one of the terminals 6 is not correctly pressed into a corresponding one of the through holes 16, as illustrated in FIG. 4A, the light emitted onto the terminal 6 is further weakened. Thus, it is extremely difficult to determine the mounting status, as illustrated in FIG. 4B. Accordingly, in view of, for example, variations in reflected light, it is difficult to set a threshold value for determining a nondefective product and a defective product. As a result, a problem occurs in that the mounting status may not be determined.

When image capturing is attempted with the intensity of illumination being increased, so to avoid the aforementioned problems, a pass/fail test may not be performed because of the amount of diffused reflection from a land increases and a captured image is whitened. Moreover, when a threshold value for the pass/fail test is decreased, the probability that a defective product is erroneously determined as being a nondefective product increases, and thus a problem occurs in the quality.

Moreover, there is mounting test for parts in which the mounting status of parts 208 mounted on the printed wiring board 14 is monitored by obtaining a surface image of the parts 208 by the use of image information obtainer 22 (e.g., a camera), as illustrated in FIG. 5. However, when large parts 202 and 206 are mounted around a small part 204, as illustrated in FIG. 6, light is cut off by the large parts 202 and 206, so that sufficient reflected light to check the mounting status may not be obtained. Thus, mounting test in which the image information obtainer 22 is used has a problem. On the other hand, recently, the packaging density of parts mounted on a printed wiring board has been increased, and thus it has become difficult to arrange, in advance, large parts so that the parts are apart from each other. In such a case, test of the mounting status needs to be performed by visual observation. Thus, a problem occurs in that individually performing visual test decreases the efficiency of test and the overall efficiency of product manufacturing.

SUMMARY

According to an aspect of the invention, a method for testing a part mounting status on a substrate, the method comprises preparing the part including a retroreflection portion for occurring reflect light by retroreflection; irradiating light onto the retroreflection portion; receiving the reflect light from the retroreflection portion; and determining whether the part exist by the use of the reflect light from the retroreflection portion.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

FIG. 6 illustrates exemplary mounting test of surface-mounted parts.

FIG. 10 illustrates the functional configuration of a mounting test device according to a second embodiment.

FIG. 11 illustrates the hardware configuration of an image processing unit.

FIG. 16 illustrates an embodiment of mounting test of parts surface-mounted on a printed wiring board.

DESCRIPTION OF EMBODIMENTS

The embodiments will be described below by referring figures.

First Embodiment

Figure 1A:
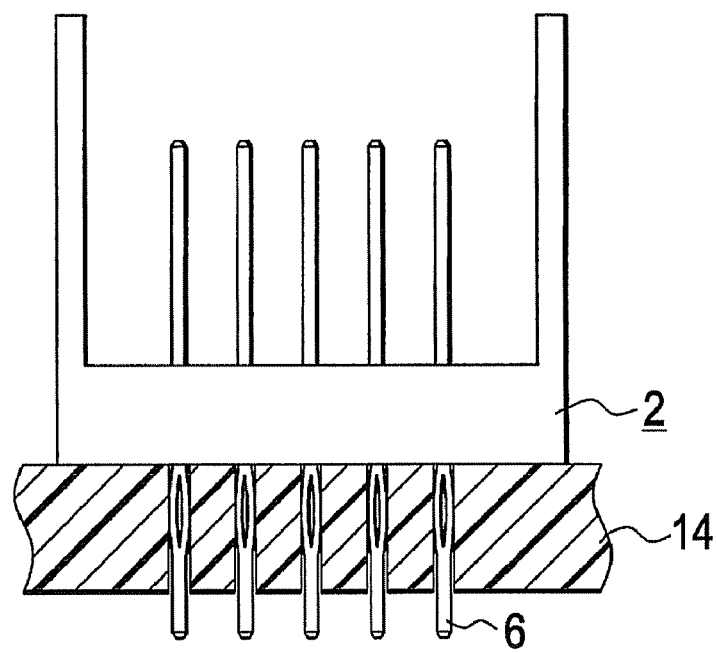
FIGS. 1A-1C illustrate exemplary known test of mounting of a press-fit connector on a printed wiring board.
Figure 1B:
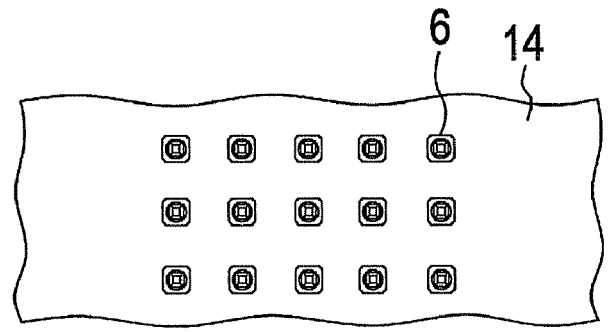
Figure 1C:
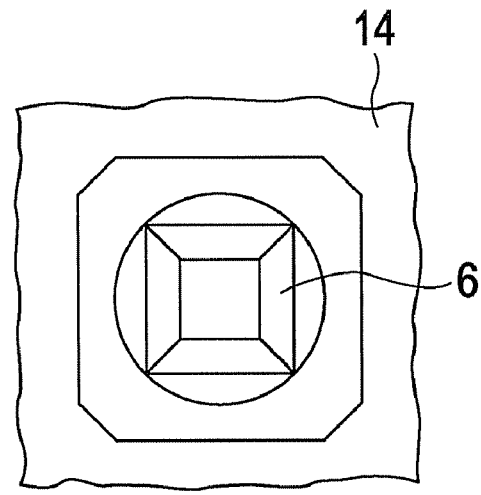
Figure 2A:
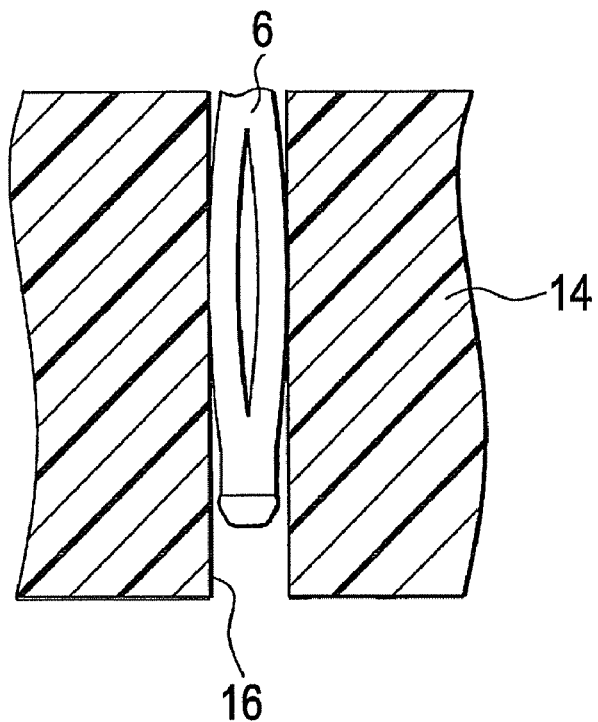
FIGS. 2A and 2B illustrate exemplary known test of mounting of a press-fit connector on a printed wiring board.
Figure 2B:
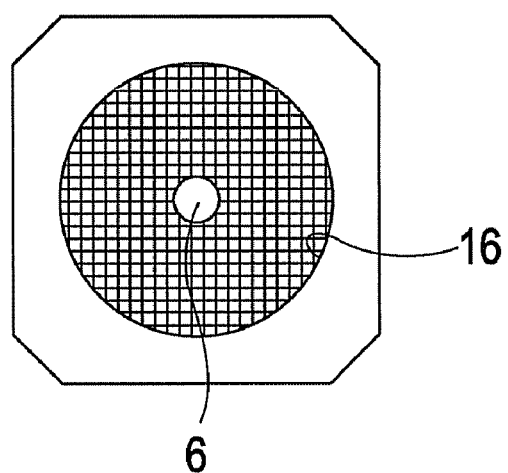
Figure 3A:
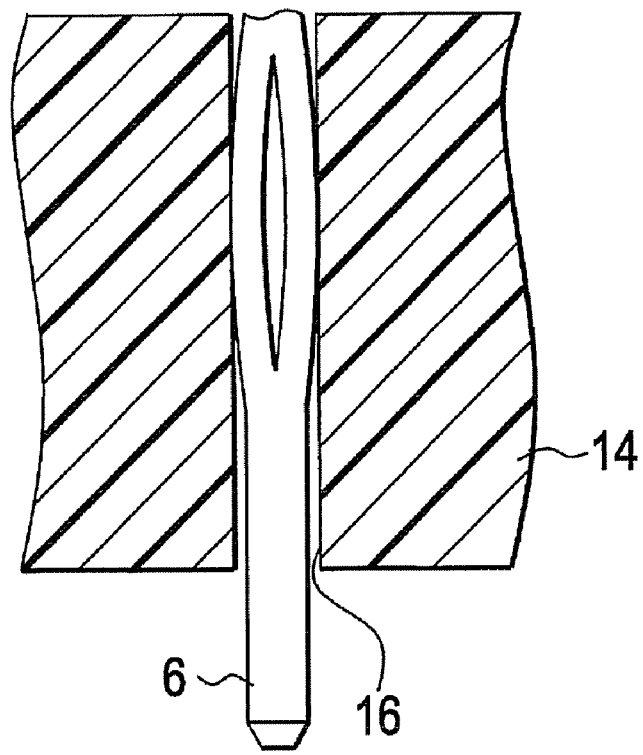
FIGS. 3A and 3B illustrate an embodiment of mounting test in a case where the tip of a terminal protrudes from the lower surface of a printed wiring board.
Figure 3B:
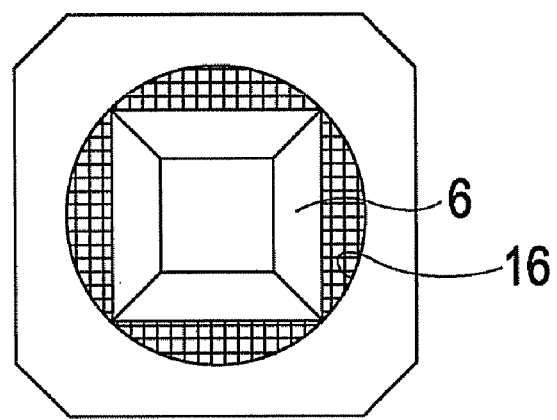
Figure 4A:
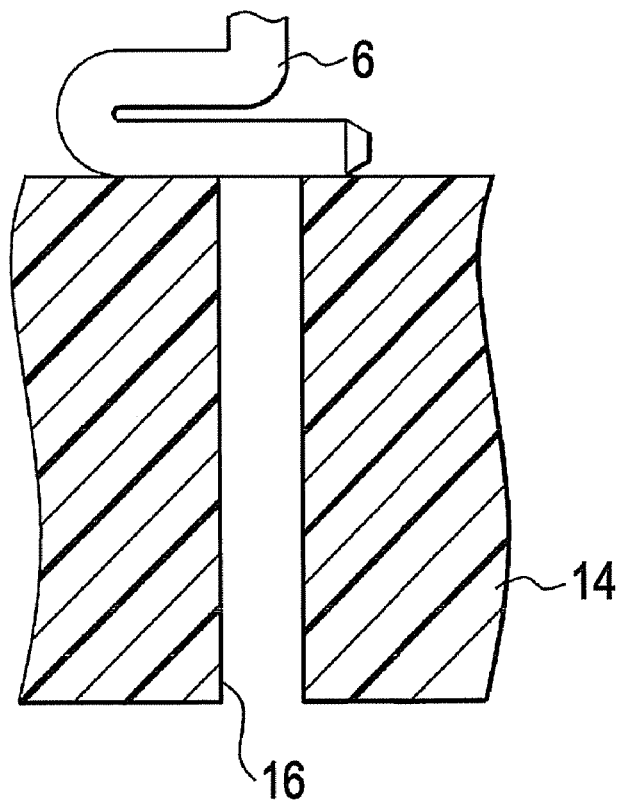
FIGS. 4A and 4B illustrate an embodiment of mounting test in a case where a terminal is buckled.
Figure 4B:
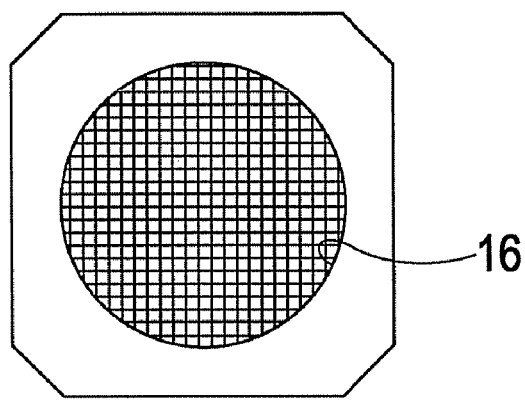
Figure 5:
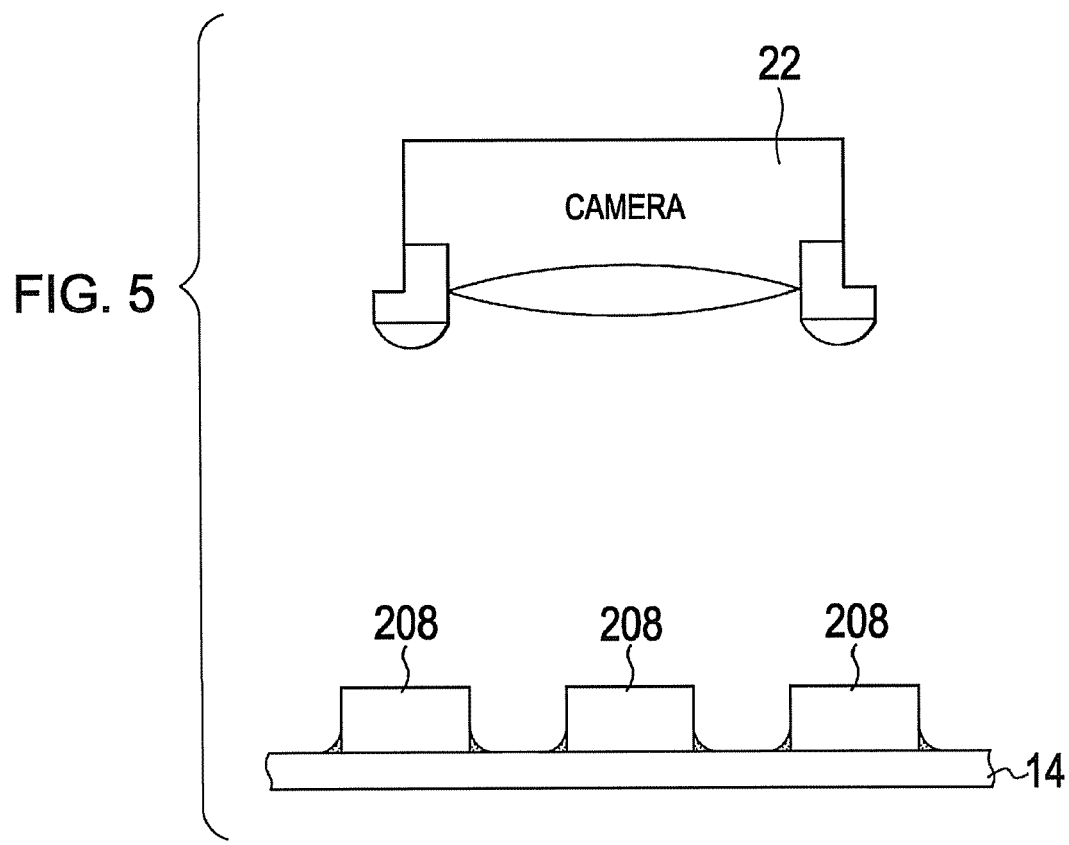
FIG. 5 illustrates exemplary mounting test of surface-mounted parts.
Figure 7A:
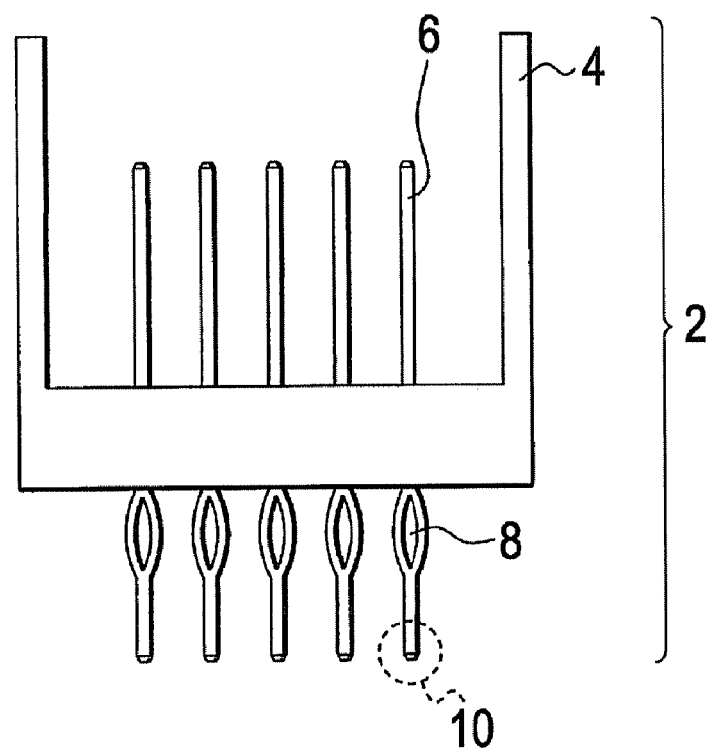
FIGS. 7A and 7B illustrate a press-fit connector according to a first embodiment.
Figure 7B:
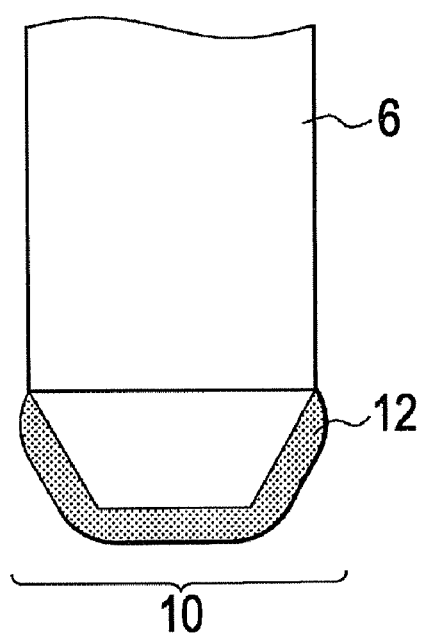
Figure 8:
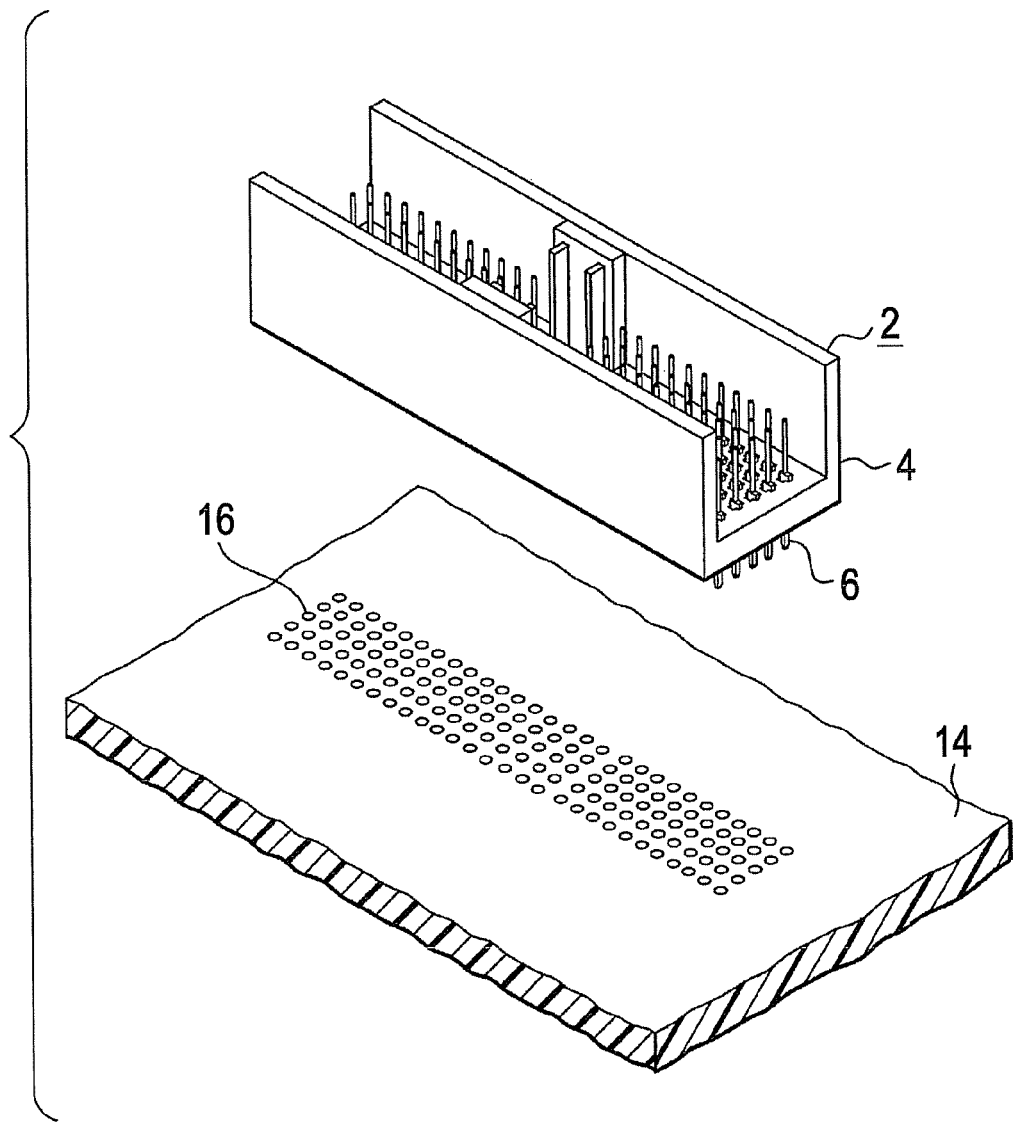
FIG. 8 illustrates the respective configurations of a press-fit connector and a printed wiring board.
Figure 9:
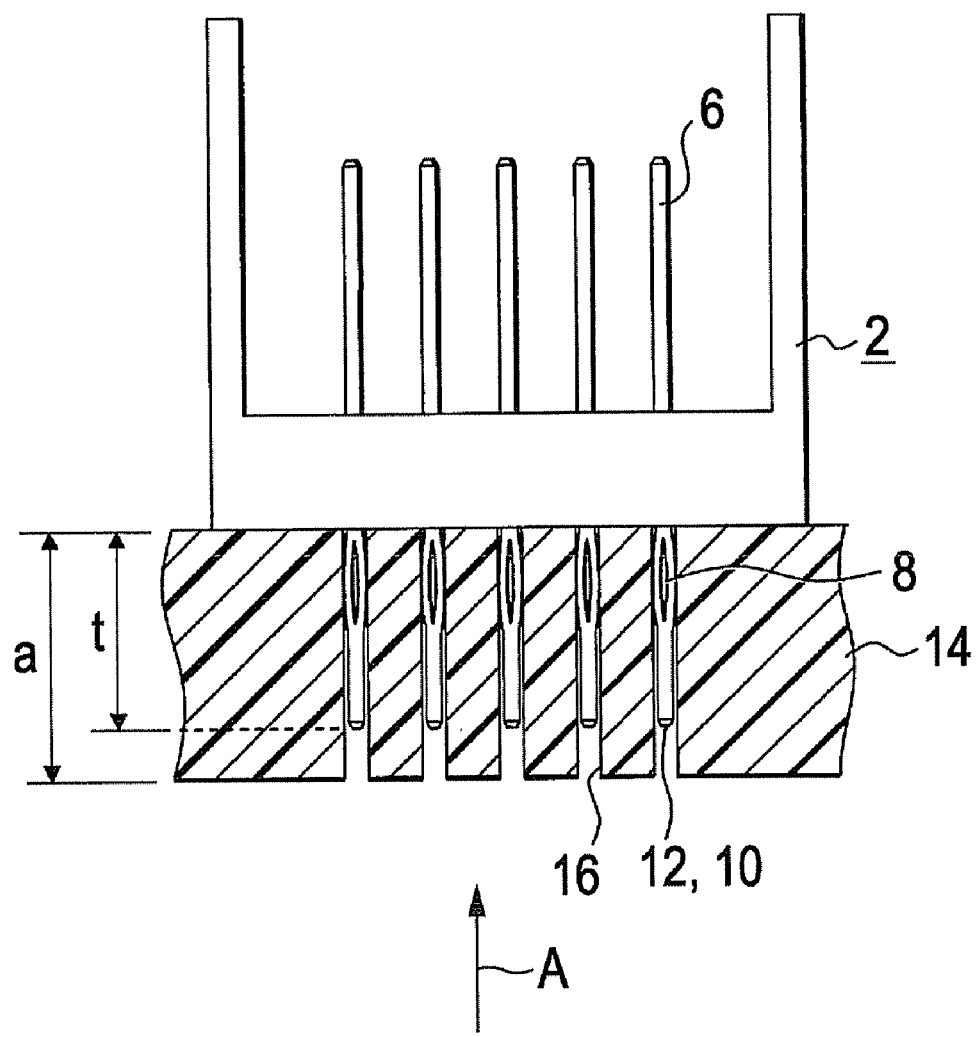
FIG. 9 illustrates the mounting status of a press-fit connector and a printed wiring board.

Parts according to a first embodiment will now be described with reference to FIGS. 7A, 7B, 8, and 9. FIGS. 7A, 7B illustrate a press-fit connector according to the first embodiment. FIG. 8 illustrates the respective configurations of the press-fit connector and a printed wiring board. FIG. 9 illustrates the mounting status of the press-fit connector and the printed wiring board. In this case, the configurations illustrated in FIGS. 7A, 7B, 8, and 9 are examples and are not restrictive.

The press-fit connector 2 as an example of a mounted part includes a housing 4 and the plurality of terminals 6, as illustrated in FIG. 7A. The terminals 6 extend through the housing 4. One end of each of the terminals 6 that protrudes from the housing 4 is connected to the printed wiring board 14 (FIG. 8) as a circuit board, and the other end is connected to, for example, another device so as to establish continuity between the device and the printed wiring board 14.

In the whole or a part of each of the terminals 6 on a side mounted on the printed wiring board 14, for example, an elliptical hollow portion 8 is provided so that the width of the terminal 6 is large. In packaging of the printed wiring board 14, when the terminal 6 of the press-fit connector 2 is pressed into a corresponding one of the through holes 16 (FIG. 8) provided in the printed wiring board 14, the hollow portion 8 receives pressure from the inner wall side of the through hole 16 toward the central axis of the terminal 6. As a result, the press-fit connector 2 and the printed wiring board 14 are brought into close contact with each other to be fixed, and continuity between the printed wiring board 14 (FIG. 9) and the terminal 6 are established.

The terminal 6 includes a retroreflective portion 12 at the tip that is a test portion 10 for checking the mounting status, as illustrated in FIG. 7B. For example, a retroreflective coating is applied to the retroreflective portion 12. For example, a coating that includes minute glass beads is used as the retroreflective coating. In the retroreflective portion 12, light incident on the tip of the terminal 6 is refracted at the glass beads included in the retroreflective coating to be reflected toward the incident direction by the action of specular reflection toward the terminal 6 as retroreflection.

As illustrated in FIG. 8, in mounting parts on the printed wiring board 14, the terminal 6 including the aforementioned hollow portion 8 is press fitted to be aligned with a predetermined position of the through hole 16 being bored through the printed wiring board 14.

In a state in which the press-fit connector 2 is mounted on the printed wiring board 14, the relationship between length t of a portion of the terminal 6 inserted into the through hole 16 in the printed wiring board 14 and thickness a of the printed wiring board 14 is: t<a, as illustrated in FIG. 9. The test portion 10 at the tip of the terminal 6 does not protrude to the lower surface side of the printed wiring board 14 and is within the through hole 16.

In test of the mounting status of the press-fit connector 2 on the printed wiring board 14, the presence or absence of the terminal 6 is checked by obtaining an image of the interior of the through hole 16 by e irradiating light onto the interior of the through hole 16 from a surface of the printed wiring board 14 opposite a surface on which the press-fit connector 2 is mounted in a direction indicated by an arrow A.

In contrast, in the press-fit connector 2, which includes the retroreflective portion 12 at the test portion 10 at the tip of the terminal 6, sufficient reflected light may be obtained, and thus sharp image information of the mounting status may be obtained.

In such an arrangement, even in a case where the tip of a terminal does not protrude from the lower surface side of a circuit board, light that enters the interior of a through hole strikes a retroreflective portion, and then light is reflected toward the incident direction, so that the mounting status may be monitored.

Second Embodiment

Regarding a mounting test device according to a second embodiment, FIGS. 10 and 11 will be referred to. FIG. 10 illustrates the functional configuration of the mounting test device according to the second embodiment. FIG. 11 illustrates the hardware configuration of an image processing unit. In this case, the configurations illustrated in FIGS. 10 and 11 are examples and are not restrictive.

A mounting test device 18 according to the second embodiment for inspecting the mounting status of the press-fit connector 2 includes, for example, light emitting part 20, image information obtainer 22, and an image processing unit 24, as illustrated in FIG. 10. The image processing unit 24 includes binarization process 26 and determination process 28. Moreover, output part 30 for outputting the result of test and the like are included. In the mounting test device 18, the light emitting part 20 irradiates light 200 onto the terminal 6 in the through hole 16 from the lower surface side of the printed wiring board 14 as a circuit board. The light 200 is retroreflected at the retroreflective portion 12 of the terminal 6, and reflected light 201 is obtained by the retroreflection. The reflected light 201 is captured with the image information obtainer 22 as light receiver. Thus, the image information of the tip of the terminal 6, which is the test portion 10, is obtained from the reflected light 201.

In the image processing unit 24, after the obtained image information is processed into binary format by the binarization process 26 as image processing, the determination process 28 determines the mounting status of the press-fit connector 2 on the basis of the image information having been subjected to binarization. Then, the output part 30 outputs the result of the determination by the determination process 28.

The light emitting part 20 includes, for example, an electric lamp, a fluorescent lamp, or a light emitting diode (LED). For example, the light emitting part 20 is arranged in one circular row or a plurality of circular rows around the image information obtainer 22. The intention of this arrangement is to irradiate light onto the interior of the through hole 16 in the printed wiring board 14 so that the terminal 6 of the mounted press-fit connector 2 can be took an image by the image information obtainer 22.

In this case, the exemplary configuration, in which the light irradiating part 20 is provided around the image information obtainer 22, is adopted due to, for example, reduction in the size of the mounting test device 18 and the characteristics of the retroreflective portion 12 provided in the terminal 6. That is, since light irradiated onto the retroreflective portion 12 is reflected toward the incident direction, the light emitting part 20 and the image information obtainer 22 are arranged to be close to each other so as to reliably capture the reflected light 201 with the image information obtainer 22.

The image information obtainer 22 includes, for example, a charge coupled device (CCD) camera. The light 200 irradiated from the light emitting part 20 is reflected at the retroreflective portion 12 of the terminal 6 in the through hole 16. Then, the image information obtainer 22 obtains the image information of the interior of the through hole 16 by receiving the reflected light 201. For example, a gray image (FIGS. 14A and 14B) described below and based on the reflected light 201 is obtained as the image information. In this case, the image information is not limited to a gray image. For example, an image, such as a picture, with which the mounting status can be visually determined may be obtained as the image information.

The binarization process 26 is image processing for determining a gray level in response to the amount of received light for each pixel by the use of the obtained image information, and for processing the pixel into one of the two colors, white and black, in a manner that depends on whether the amount of received light is equal to or more than or equal to or less than a predetermined threshold value. Thus, for example, a portion of the image information where the amount of the reflected light 201 having been received is large is whitened.

The determination process 28, together with the binarization process 26, is included in the image processing unit 24. Regarding binarized image information by the binarization process 26, the determination process 28 performs determination for each pixel so as to determine the presence or absence of a part from the number of pixels in a white portion. That is, when the amount of the reflected light 201 from the retroreflective portion 12 is large, the binarized image information includes a large white portion. A large amount of the reflected light 201, out of the light 200 irradiate toward the interior of the through hole 16, is recognized when the terminal 6 including the retroreflective portion 12 exists in the through hole 16. Thus, in the determination process 28, when it is determined that the amount of a white portion is larger than a predetermined threshold value, it can be determined that the terminal 6 is normally mounted.

Moreover, in a mounting operation, when the terminal 6 is not normally mounted because, for example, the terminal 6 is buckled, since the reflected light 201 from the interior of the through hole 16 can hardly be obtained, binarized image information includes a large black portion.

The output part 30 performs, for example, an operation of displaying, on a monitor or the like, information indicating whether each of the terminals 6 having been subjected to mounting test is a nondefective product or a defective product on the basis of the determination result of the mounting status determined by the determination process 28. Moreover, the output part 30 may perform an output operation by the use of, for example, warning lights in different colors indicating a nondefective product and a defective product, or the output part 30 may output a voice notice upon determining a defective product.

Regarding an example of the hardware configuration of the image processing unit 24, which performs image processing as well as operational control of the mounting test device 18, FIG. 11 will be referred to.

The image processing unit 24 includes, for example, a computer and includes a central processing unit (CPU) 32, a random access memory (RAM) 34, an input and output (I/F) unit 36, a storage unit 38, a display unit 40, and the like.

The CPU 32 is for executing, for example, arithmetic processing such as binarization and determination by the use of, an operating system (OS) that controls the basic operation, operational control programs for controlling the light emitting part 20 or the image information obtainer 22, and operational control programs such as a program for binarizing image information and a determination program. The CPU 32 also receives or transfers data from or to the storage unit 38 and controls individual functional components. The RAM 34 is a work area for executing the aforementioned computing and the like and constitutes the binarization process 26 (FIG. 10), the determination process 28 (FIG. 10), and the like by causing individual operational control programs described below and the like to operate.

The I/F unit 36 is input and output part that is connected to, for example, the light emitting part 20 and the image information obtainer 22 provided outside the image processing unit 24 so as to receive image information and sends operation instructions. Moreover, for example, the I/F unit 36 may be connected to another control computer, a device for packaging a printed wiring board, and the like and send the result of mounting test.

The storage unit 38 stores, for example, a control program such as an OS, a binarization program 42 for binarizing a gray image obtained from the image information obtainer 22, and a determination program 44 for determining the presence or absence of a part by determining whether, regarding binarized image information, the number of pixels in a white portion is larger than a threshold value. Moreover, the storage unit 38 may store, for example, a display program for displaying, on the basis of the determination result, the determination on, for example, the display unit 40.

The display unit 40 is the aforementioned output part 30 and includes, for example, a display such as a liquid crystal display (LCD).

The image processing unit 24 may include, for example, operation input part for receiving operation instructions from the outside.

Figure 12A:
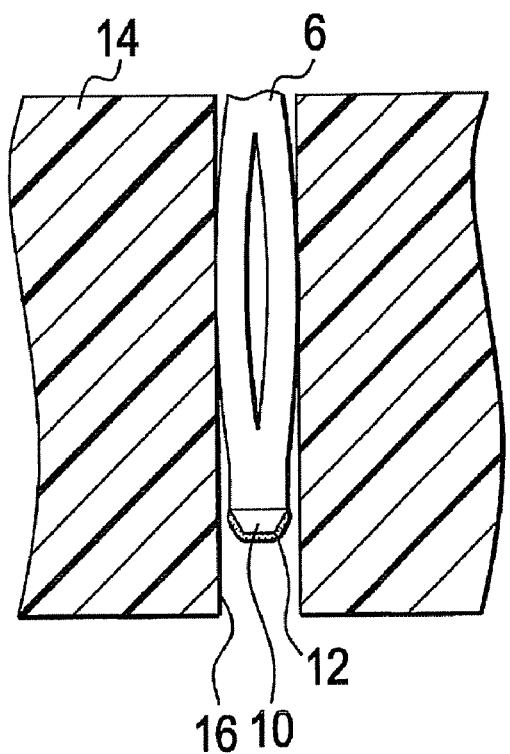
FIGS. 12A and 12B illustrate an example in a case where the mounting status of a press-fit connector and a printed wiring board is that of a nondefective product.
Figure 12B:
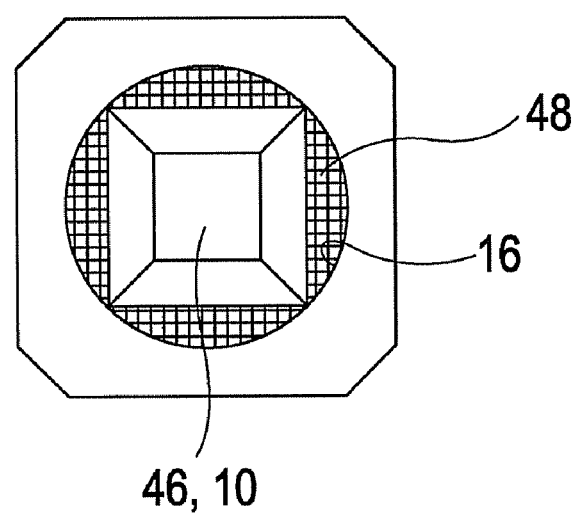
Figure 13:
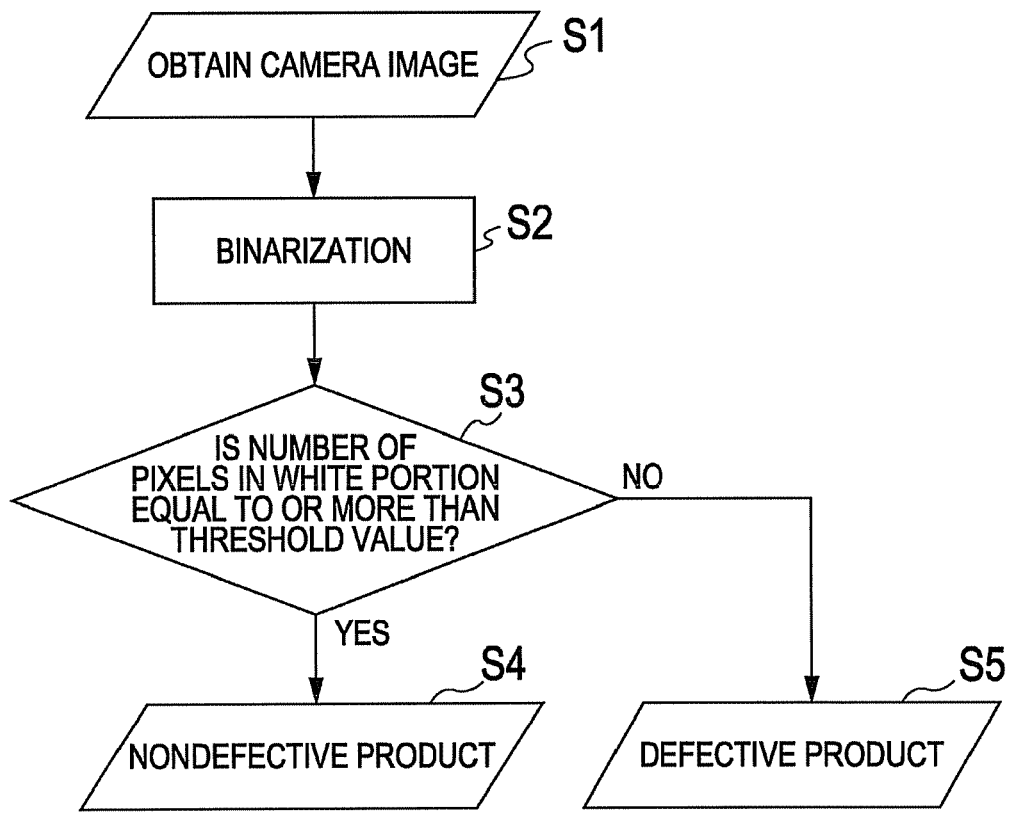
FIG. 13 is a flowchart illustrating a pass/fail test of the mounting status of a press-fit connector.
Figure 14A:
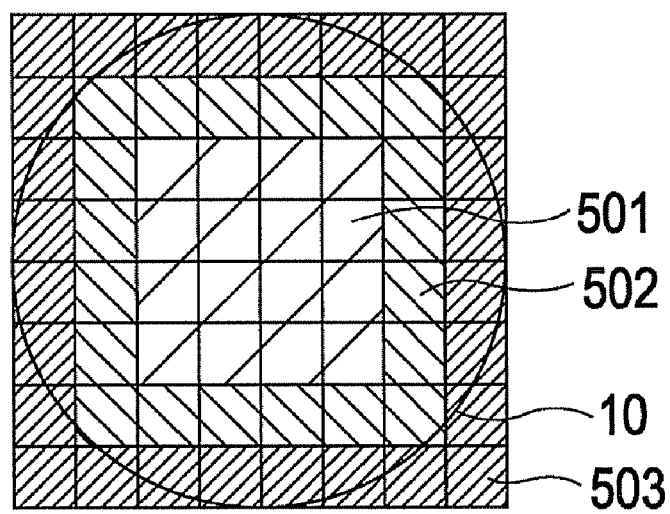
FIGS. 14A and 14B illustrate gray image information obtained by image information obtainer.
Figure 14B:
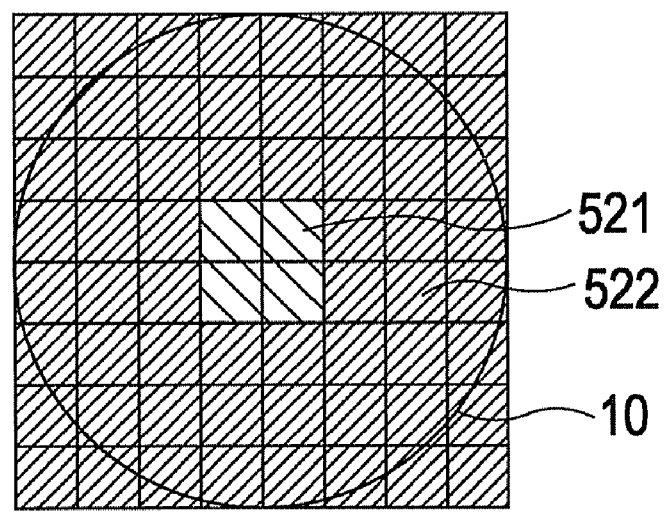
Figure 15A:
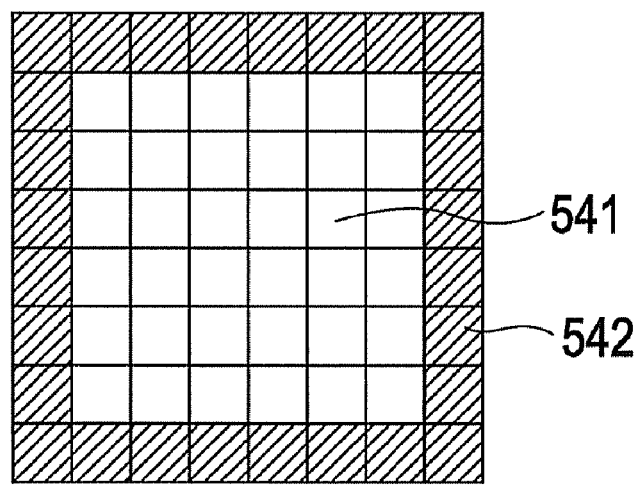
FIGS. 15A and 15B illustrate an example in which a gray image is binarized.
Figure 15B:
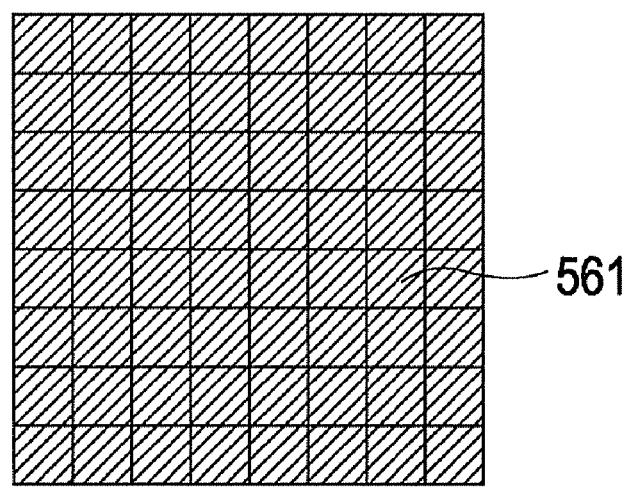

Regarding the individual operations of a mounting test method and a mounting test program for a printed wiring board as a circuit board, FIGS. 12A, 12B, 13, 14A, 14B, 15A and 15B will be referred to. FIGS. 12A and 12B illustrates an example in a case where the mounting status of a press-fit connector and a printed wiring board is that of a nondefective product. FIG. 13 is a flowchart illustrating a pass/fail test of the mounting status of a press-fit connector. FIGS. 14A and 14B illustrate gray image information obtained by image information obtainer. FIGS. 15A and 15B illustrate an example in which a gray image is binarized. In this case, the configurations and operations illustrated in FIGS. 12A, 12B, 13, 14A, 14B and 15 are examples and are not restrictive.

In the mounting test method, automatic test is performed by the use of an image of the tip of the terminal 6 that is the test portion 10 of the press-fit connector 2 having been press-fit. Light of the light emitting part 20 (FIG. 10) is irradiated onto the printed wiring board 14 from the lower surface thereof to capture an image of the test portion 10 of the terminal 6 of the press-fit connector 2 pressed into the printed wiring board 14 with a CCD camera of the image information obtainer 22. Each pixel of the obtained gray image information is processing in binarization. When the number of pixels in a white portion of the binarized image is equal to or more than a predetermined value, it is determined that the terminal 6 is a nondefective product.

In FIG. 12A, in the terminal 6 as being a nondefective product, sharp image information of the mounting status can be obtained due to the retroreflective portion 12 provided at the test portion 10 at the tip, as illustrated. When the image information is binarized, a portion 48 indicated by hatching is a black portion, and a portion 46 indicated in outline is a white portion, as illustrated in a binarized image in FIG. 12B. A circle in FIG. 12B illustrates the shape of the through hole 16. Regarding the terminal 6 that is determined as being a nondefective product, in the through hole 16, the number of pixels in the white portion 46 is larger than the number of pixels in the black portion 48. In contrast, regarding the terminal 6 that is determined as being a defective product, the image information of the terminal 6 may not be obtained because, for example, buckling appears in the terminal 6 due to a small bend or the like when the terminal 6 is press-fit. Thus, in a binarized image of the interior of the through hole 16, only the black portion 48 appears, or the white portion 46, which is infinitesimally small, appears. The number of pixels in the white portion 46 that is the boundary between a nondefective product and a defective product is determined by tests and the like to be set as a threshold value. When the number of pixels in the white portion 46 is equal to or more than the threshold value, the terminal 6 is determined as being a nondefective product, and when the number of pixels in the white portion 46 is less than the threshold value, the terminal 6 is determined as being a defective product.

The pass/fail test in the mounting test will now be described with reference to the flowchart in FIG. 13.

The image processing unit 24 obtains, from the image information obtainer 22, image information captured by shooting the interior of the through hole 16 from the lower surface side of the printed wiring board 14 (S1). The image information that can be obtained in this case is obtained as a gray image of each pixel, as illustrated in FIGS. 14A and 14B. The shading of each pixel is expressed by, for example, gray levels ranging from 0 to 255. In this case, a gray image 50 illustrated in FIG. 14A is an example in a case where the mounting status is that of a nondefective product. In FIG. 14A, there are three gray levels 501 to 503. A gray image 52 illustrated in FIG. 14B is an example in a case where the mounting status is that of a defective product. In FIG. 14B, there are two gray levels 521 and 522.

Then, the gray image is binarized for each pixel (S2). In the binarization, each pixel is subjected to image processing into white or black in response to a gray level due to difference in the amount of received light. For example, assuming that a threshold value is 128, pixels having gray levels ranging from 0 to 127 constitute a black portion, and pixels having gray levels ranging from 128 to 255 constitute a white portion. FIGS. 15A and 15B illustrate an example of an image obtained by binarizing the gray image. FIG. 15A illustrates an example of a binarized image 54 in a case where the mounting status is that of a nondefective product. In this case, 501 and 502 in FIG. 14A constitute a white portion 541, and 503 in FIG. 14A constitutes a black portion 542. FIG. 15B illustrates an example of a binarized image 56 in a case where the mounting status is that of a defective product. In this case, 521 and 522 in FIG. 14B constitute a black portion 561. In the binarized image 54 of a nondefective product, a white portion is large due to the reflected light 201 from the retroreflective portion 12 provided in the terminal 6. In contrast, the binarized image 56 of a defective product is a black image as a whole because the reflected light 201 is hardly obtained.

After the binarization, the process proceeds to the pass/fail test of the mounting status (S3). In the pass/fail test, it is determined whether the number of pixels in a white portion is equal to or more than a predetermined threshold value. In this case, when a threshold value serving as a judgment criterion is set to 28, for example, the number of pixels in a white portion, out of the number of all pixels in the binarized image 54, is 36, as illustrated in FIG. 15A, and thus it is determined that the terminal 6 is a nondefective product because $36 \geqq 28$ (the threshold value). Moreover, in the binarized image 56 illustrated in FIG. 15B, the number of pixels in a white portion is 0. Thus, it is determined that the terminal 6 is a defective product because 0<28 (the threshold value).

In this manner, in a binarized image, when the number of pixels in a white portion is equal to or more than the threshold value (YES in S3), it is determined that the terminal 6 is a nondefective product (S4), and when the number of pixels in a white portion is less than the threshold value (NO in S3), it is determined that the terminal 6 is a defective product (S5). The result of determining a nondefective product or a defective product is output to, for example, the output part 30 (the display unit 40 or the like) in the mounting test device 18.

According to such an arrangement, the vertical component of illumination light, ambient light, and the like irradiated onto a retroreflective portion provided at a test portion can be reflected toward a camera of image information obtainer, and thus, even when light irradiated onto a part to be inspected is weak, a sharp image may be obtained. Moreover, even when the tip of a terminal of a press-fit connector does not protrude from the lower surface of a circuit board, the mounting status may be inspected. Moreover, when a mounting test device for inspecting the mounting status by the use of an image is used, mounting test may be performed by providing a retroreflective portion in a terminal to be inspected. Thus, renovation of extensive facility may be inexpensive.

Third Embodiment

Regarding a third embodiment, FIG. 16 will be referred to. FIG. 16 illustrates an embodiment of mounting test of parts surface-mounted on a printed wiring board. In this case, the arrangement of mounting test illustrated in FIG. 16 is an example and is not restrictive. Moreover, in FIG. 16, the same reference numerals are assigned to components similar to those in the aforementioned embodiment, and the description is omitted.

In the aforementioned embodiment, mounting test is performed by checking the presence or absence of the terminal 6 as a part pressed into the through hole 16 of the printed wiring board 14 serving as a circuit board. On the other hand, in mounting test of parts on the printed wiring board 14 according to this embodiment, the test portion 10 is provided at the exterior portion of a mounted part.

For example, parts 202 (A), 204 (B), and 206 (C) are surface-mounted on the printed wiring board 14. The height of the part 204 in a mounted state is lower than the height of the parts 202 and 206 in a mounted state. Moreover, the density of disposed parts is high.

In mounting test of the part 204, it is assumed that the exterior portion of the part is the test portion 10. Then, the retroreflective portion 12 is provided at the test portion 10 as the exterior portion of the part 204. For example, a retroreflective coating is applied to the retroreflective portion 12.

The mounting test device 18, which inspects the mounting status, is similar to that in the aforementioned embodiment and includes, for example, the light emitting part 20, the image information obtainer 22, the image processing unit 24, and the output part 30. The image information obtainer 22 captures reflected light from the retroreflective portion 12 in response to light irradiated from the light emitting part 20, the image information of the mounting status is captured with, for example, a CCD camera, and the mounting status is determined from a binarized image depending on the shading of the image information. In the binarization and the determination, operations similar to those in the aforementioned embodiment are performed. Thus, the detailed description is omitted.

In a mounting test method in which light is emitted onto the mounting surface side, and the reflected light is used, the part 204 is covered by the shadows of the parts 202 and 206, and thus it is difficult to capture reflected light, as described above. In contrast, according to the just described arrangement, since the retroreflective portion 12 is provided on the part 204, the retroreflective portion 12 retroreflects light from the light emitting part 20, and the reflected light is captured. Thus, since the image information of the mounting status is obtained, mounting test may be performed.

Fourth Embodiment

Figure 17A:
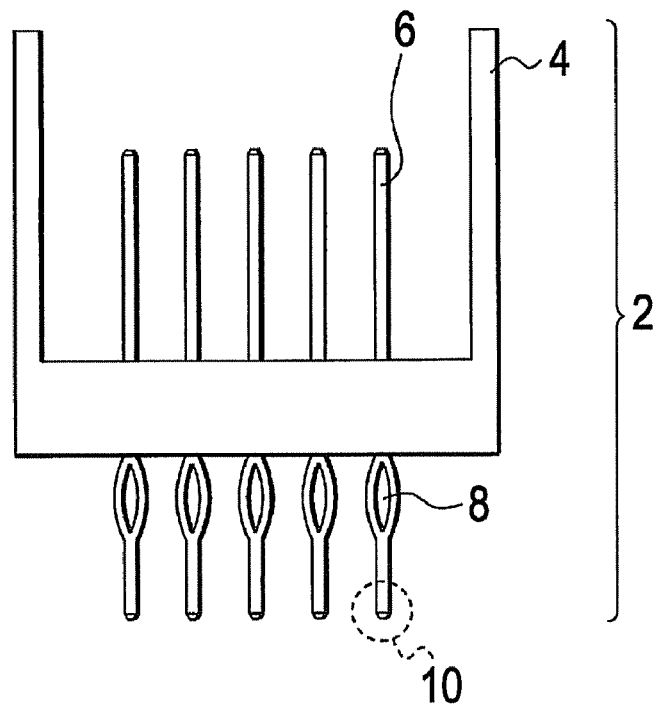
FIGS. 17A and 17B illustrate a press-fit connector according to a fourth embodiment.
Figure 17B:
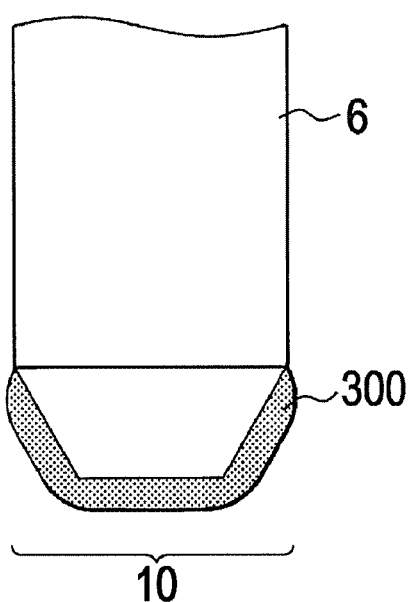
Figure 18:
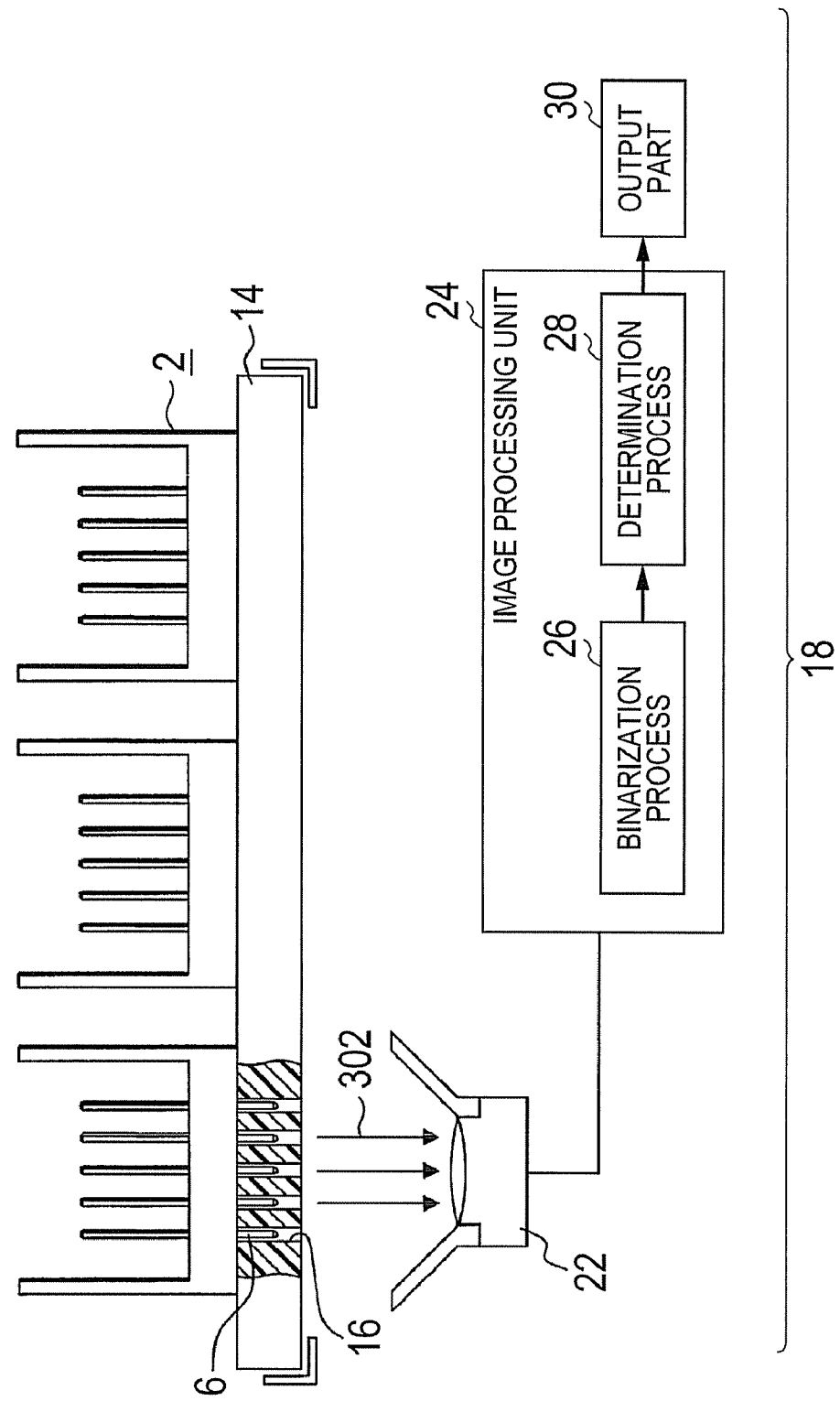
FIG. 18 illustrates the functional configuration of a mounting test device according to the fourth embodiment.

Regarding a part and a mounting test method and a mounting test device for the part according to a fourth embodiment, FIGS. 17A, 17B and 18 will be referred to. FIGS. 17A and 17B illustrate a press-fit connector according to the fourth embodiment. FIG. 18 illustrates the functional configuration of the mounting test device according to the fourth embodiment. In FIGS. 17A, 17B and 18, the same reference numerals are assigned to components equivalent to those in FIGS. 7A to 11, and the description is omitted. Moreover, the configurations illustrated in FIGS. 17A, 17B and 18 are examples and are not restrictive.

In this embodiment, a self-luminous portion 300 is provided at the test portion 10 where the mounting status of the press-fit connector 2 as an example of a part is determined. In this case, for example, a luminous coat, such as a luminous paint, that stores light energy such as ultraviolet rays or a fluorescent coating is applied to the self-luminous portion 300. Since the test portion 10 emits light, as illustrated in FIG. 17B, the mounting test device 18 does not include the light emitting part 20.

In mounting test of the press-fit connector 2 including the self-luminous portion 300, an image of the test portion 10 is captured with the image information obtainer 22 by the use of light 302 emitted by the self-luminous portion 300 (FIGS. 17A and 17B), as illustrated in FIG. 18. Then, the obtained image information is subjected to image processing, as described above, and the mounting status is determined.

In this embodiment, an exemplary configuration in which the mounting test device 18 does not include the light emitting part 20 has been described. However, apart from this configuration, light emitting part for storing ultraviolet rays or the like in the luminous paint or the like of the self-luminous portion 300 may be provided.

Even in such an arrangement, since the image information of a portion to be tested may be obtained from light emitted by a self-luminous portion, mounting test of a part may be performed.

Figure 19:
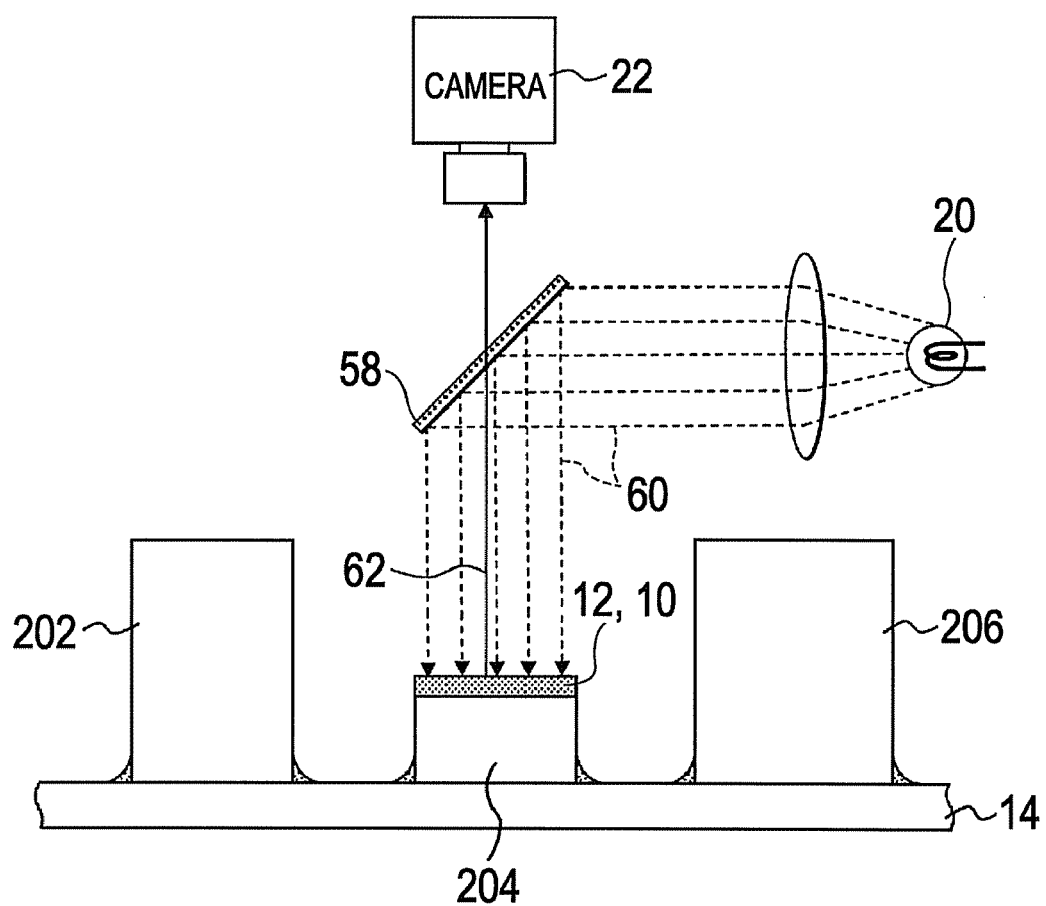
FIG. 19 illustrates the configuration of a mounting test device according to another embodiment.

Transformative Example of Embodiments (1) In the aforementioned embodiments, regarding the light emitting part 20, according to characteristics such that light irradiated onto the retroreflective portion 12 is reflected toward the incident direction, the light emitting part 20 is provided around the image information obtainer 22. However, apart from the aforementioned embodiments, for example, coaxial epi-illumination in which a half mirror 58 is used may be used, as illustrated in FIG. 19.

According to coaxial epi-illumination, light 60 emitted by the light emitting part 20 is irradiated onto the retroreflective portion 12 of the part 204 along the same axis as a camera that is the image information obtainer 22 by being reflected by the half mirror 58, which reflects light incident from a predetermined direction. Then, the light 60 irradiated onto the retroreflective portion 12 is reflected toward the image information obtainer 22 by the action of retroreflection described above. At this time, since the half mirror 58 passes reflected light 62, the image information obtainer 22 obtain the image information of the test portion 10 of the part 204.

According to such an arrangement, the size of components around the image information obtainer 22, such as a CCD camera, may be reduced. Moreover, the mounting test position may be changed by changing the emission position by moving the light emitting part 20 and accordingly changing the orientation of the half mirror 58. Thus, mounting test in response to the placement of a mounted part on the printed wiring board 14 may be performed.

(2) Moreover, in the surface mounting test according to the aforementioned embodiments, other than a case where test cannot be performed because parts having different heights are closely packed, for example, according to the importance or the like of each mounted part, the retroreflective portion 12 may be provided in an predetermined mounted part. Moreover, for example, in a case where positions where parts are mounted are concentrated, the retroreflective portion 12 or the self-luminous portion 300 may be provided for a part for which a mounting error is highly likely to occur. According to such an arrangement, the discovery rate of mounting errors may be improved.

Features, advantages, and the like of the embodiments having been described will now be listed.

(1) A retroreflective portion or a self-luminous portion is provided for a part the mounting status of which is inspected. Thus, even when light irradiated onto a part to be inspected is weak, the vertical component of illumination light and ambient light irradiated onto the retroreflective portion is reflected toward a CCD camera, so that the reflected light may be captured, or self luminescence may be received by a CCD camera. Thus, a sharp image may be obtained.

(2) When a retroreflective coating is used as a retroreflective portion, the retroreflective portion may be readily provided in a part to be inspected. Moreover, when a luminous paint is used as a self-luminous portion, the self-luminous portion may be provided in a similar manner.

(3) Since a retroreflective portion or a self-luminous portion is provided in a part to be inspected, even when the tip of a terminal of a press-fit connector does not protrude from the lower surface of a printed wiring board, mounting test may be performed.

(4) Moreover, when, in the packaging process for a printed wiring board, mounting test may not be performed because the tip of a terminal of a press-fit connector does not protrude from the lower surface of a printed wiring board, and thus the printed wiring board, the packaging of which is defective, is distributed and when a defective condition is detected in an electrical functional test after the packaging process, many man-hours are necessary to locate and repair a defective portion. However, according to the aforementioned arrangements of the embodiments, such man-hours may be eliminated.

(5) Regarding a mounting test device in a case where the tip of a terminal of a press-fit connector does not protrude from the lower surface of a printed wiring board, renovation of existing test facilities such as a CCD camera may be inexpensive.

(6) In evaluations before mass production is started, when a retroreflective coating or a luminous paint is applied to the tip of a terminal of a press-fit connector in a simple manner, since the accuracy of test of the mounting status is improved, the efficiency of evaluation of mass production may be improved.

(7) When a retroreflective coating, a luminous paint, or the like is applied to the exterior portion of a surface-mounted part surrounded by tall parts in advance, mounting test may be performed in the same way as described above. Thus, the efficiency of test may be improved.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A method for testing a part mounting status on a substrate, the method comprising:
    preparing the part including a printed circuit board mounting a terminal inserted into a hole on the printed circuit board, a retroreflection portion which causes light to be reflected by retroreflection being arranged on a tip of the terminal to be inserted into the hole, the retroreflection portion including retroreflection paint;
    irradiating light onto the retroreflection portion so as to obtain a reflected light caused by the retroreflection portion when the tip positions between ends of the hole;
    receiving the reflected light; and
    determining a mounting status of the part by the use of the received, reflected light.

2. The method of claim 1, wherein the part is a press-fit connector.

3. The method of claim 1, wherein the determining includes:
    obtaining image information by the use of the received, reflected light;
    executing image processing of the obtained image information; and
    determining whether a number of pixels in the image processed, obtained image information having a predetermined color is larger than a threshold value.

4. The method of claim 3, wherein
    the image processing is a binarization process, and
    the predetermined color is white.

5. The method of claim 1, wherein the irradiating uses coaxial epi-illumination.

6. A method for testing a part mounting status on a substrate, the method comprising:
    preparing the part including a printed circuit board mounting a terminal inserted into a hole on the printed circuit board, a self-luminous portion for luminescing light being arranged on a tip of the terminal to be inserted into the hole, the self-luminous portion including luminous paint;
    receiving the light luminescing from the self-luminous portion when the tip positions between ends of the hole; and
    determining a mounting status of the part by the use of the received light.

7. The method of claim 6, wherein the part is a press-fit connector.

8. The method of claim 6, wherein the determining includes:
    obtaining image information by the use of the received light;
    executing image processing of the obtained image information; and
    determining whether a number of pixels in the image processed, obtained image information having a predetermined color is larger than a threshold value.

9. The method of claim 8, wherein
    the image processing is a binarization process, and
    the predetermined color is white.

10. A method comprising:

providing a printed circuit board having first and second sides and a hole passing through the printed circuit board from the first side to the second side, and having a terminal of a part inserted into the hole from the first side so that at least a portion of the terminal is in the hole, the terminal having a tip with an retroreflection portion including retroreflection paint, and a length of said at least a portion of the terminal in the hole being less than the thickness of the printed circuit board so that the terminal does not protrude from the second side of the printed circuit board;

irradiating light into the hole from the second side of the printed circuit board so that the light is incident on the retroreflection portion which thereby causes the incident light to be reflected by the retroreflection portion;

receiving the reflected light through the hole from the second side of the printed circuit board; and determining a mounting status of the part by the use of the reflected light.

11. A method comprising:

providing a printed circuit board having first and second sides and a hole passing through the printed circuit board from the first side to the second side, and having a terminal of a part inserted into the hole from the first side so that at least a portion of the terminal is in the hole, the terminal having a tip with a self-luminous portion including luminous paint luminescing light, and a length of said at least a portion of the terminal in the hole being less than the thickness of the printed circuit board so that the terminal does not protrude from the second side of the printed circuit board;

receiving the luminescing light through the hole from the second side of the printed circuit board; and determining a mounting status of the part by the use of the received luminescing light.

\* \* \* \* \*